United States Patent
Ho

(10) Patent No.: US 10,602,970 B2
(45) Date of Patent: Mar. 31, 2020

(54) GLUCOSE TEST DEVICE

(71) Applicant: SKYLA CORPORATION HSINCHU SCIENCE PARK BRANCH, Hsinchu (TW)

(72) Inventor: Szu-Hsien Ho, Taipei (TW)

(73) Assignee: SKYLA CORPORATION HSINCHU SCIENCE PARK BRANCH, Hsinchu (TW)

( * ) Notice: Subject to any disclaimer, the term of this patent is extended or adjusted under 35 U.S.C. 154(b) by 822 days.

(21) Appl. No.: 14/840,060

(22) Filed: Aug. 31, 2015

(65) Prior Publication Data

US 2016/0128614 A1    May 12, 2016

(30) Foreign Application Priority Data

Nov. 7, 2014   (TW) .............................. 103138744 A

(51) Int. Cl.
| | | |
|---|---|---|
| A61B 5/151 | (2006.01) | |
| A61B 5/15 | (2006.01) | |
| A61B 5/157 | (2006.01) | |
| H01H 13/14 | (2006.01) | |

(52) U.S. Cl.
CPC .......... *A61B 5/1518* (2013.01); *A61B 5/157* (2013.01); *A61B 5/150022* (2013.01); *A61B 5/15113* (2013.01); *A61B 5/15115* (2013.01); *A61B 5/15117* (2013.01); *A61B 5/15151* (2013.01); *A61B 5/15163* (2013.01); *A61B 5/15182* (2013.01); *A61B 5/150358* (2013.01); *A61B 5/150412* (2013.01); *H01H 13/14* (2013.01); *A61B 5/150183* (2013.01)

(58) Field of Classification Search
None
See application file for complete search history.

(56) References Cited

U.S. PATENT DOCUMENTS

| | | | | |
|---|---|---|---|---|
| 3,626,929 | A * | 12/1971 | Sanz ................ | A61B 5/150022 600/583 |
| 8,292,826 | B1 * | 10/2012 | Shaanan ............ | A61B 5/14532 600/575 |
| 2006/0052724 | A1 * | 3/2006 | Roe .................... | A61B 5/14532 600/583 |
| 2010/0198107 | A1 * | 8/2010 | Groll ................ | A61B 5/150022 600/583 |
| 2011/0270061 | A1 * | 11/2011 | Say ..................... | A61B 5/1411 600/345 |

* cited by examiner

*Primary Examiner* — Matthew Kremer
(74) *Attorney, Agent, or Firm* — JCIPRNET

(57) ABSTRACT

A glucose test device includes a casing, a carrying unit, consumables, a first push rod, a locking component, a first driving unit and a control unit. The carrying unit is disposed at the casing. The consumables are disposed in the carrying unit. The first push rod is movably disposed at the casing. The first push rod is suitable for moving to push one consumable out of the carrying unit. The locking component is movably disposed at the casing. The first driving unit is connected to the locking component. The control unit is electrically connected to the first driving unit. The control unit is suitable for controlling the first driving unit to drive the locking component to lock the first push rod as unmovable. The control unit is suitable for controlling the first driving unit to drive the locking component to release the first push rod.

13 Claims, 15 Drawing Sheets

GLUCOSE TEST DEVICE

CROSS-REFERENCE TO RELATED APPLICATION

This application claims the priority benefit of Taiwan application serial no. 103138744, filed on Nov. 7, 2014. The entirety of the above-mentioned patent application is hereby incorporated by reference herein and made a part of this specification.

BACKGROUND OF THE INVENTION

Field of the Invention

The invention relates to a test device, and particularly to a glucose test device.

Description of Related Art

As technology advances and health consciousness rises, the public pay more and more attention to health care related issues. Accordingly, medical equipment has continued to evolve and improve in order to satisfy both manufacturing specifications for the medical equipment and the demand of the public.

In terms of glucose testing, for example, several different types of lancing devices, such as lancing pens, lancets or lancing tubes, etc., have been derived. Most lancing devices currently on the market include a glucose meter in combination with bulk-packed lancets and test strips. Therefore, during the use, a user has to manually install a lancet and a test strip, and after a blood sample and a test result are obtained, the user has to manually remove the used lancet and test strip and reinstall a brand-new lancet and a brand-new test strip for next use. In this way, although the user is free from health and testing concerns, such as bacterial infection or cross infection by blood, caused by repeated use of the lancet and the test strip, the installation steps of the lancet and the test strip are complicated, thereby causing the user great inconvenience in operation.

SUMMARY OF THE INVENTION

The invention provides a glucose test device easy to operate and capable of preventing a user from firing a lancet in an unexpected operation condition.

The glucose test device of the invention includes a casing, a carrying unit, a plurality of consumables, a first push rod, a locking component, a first driving unit and a control unit. The carrying unit is disposed at the casing. The consumables are disposed in the carrying unit. The first push rod is movably disposed at the casing and is aligned with the carrying unit. The first push rod is suitable for moving to push one of the consumables out of the carrying unit. The locking component is movably disposed at the casing. The first driving unit is connected to the locking component. The control unit is electrically connected to the first driving unit. The control unit is suitable for controlling the first driving unit to drive the locking component to be operated to a locking position so as to lock the first push rod as unmovable. The control unit is suitable for controlling the first driving unit to drive the locking component to be operated to a releasing position so as to release the first push rod.

In an embodiment of the invention, the first driving unit includes a motor and a gear set. The gear set is connected between the motor and the locking component. The motor is suitable for driving the gear set to operate so as to drive the locking component to be operated to the locking position or the releasing position.

In an embodiment of the invention, the glucose test device includes a second push rod, wherein the second push rod is movably disposed at the casing and is aligned with the carrying unit. The second push rod is connected to the first driving unit. When the consumables include a plurality of lancets and a plurality of test strips, the first push rod is suitable for moving to push one of the lancets out of the carrying unit, and the first driving unit is suitable for driving the second push rod to move toward the carrying unit so as to push one of the test strips out of the carrying unit.

In an embodiment of the invention, the glucose test device includes a second push rod, wherein the second push rod is movably disposed at the casing and is aligned with the carrying unit. The second push rod is connected to the first driving unit. When the consumables include only a plurality of lancets, the first push rod is suitable for moving to push one of the lancets out of the carrying unit, and the first driving unit does not drive the second push rod to move toward the carrying unit.

In an embodiment of the invention, the glucose test device includes a second push rod, wherein the second push rod is movably disposed at the casing and is aligned with the carrying unit. The second push rod is connected to the first driving unit. When the consumables include only a plurality of test strips, the first driving unit is suitable for driving the second push rod to move toward the carrying unit so as to push one of the test strips out of the carrying unit, and the locking component remains at the locking position.

In an embodiment of the invention, the first driving unit has a protrusion. The protrusion moves synchronously with the second push rod. The locking component has a driven portion. When the protrusion moves into a first moving range to be misaligned with the driven portion, the locking component is located at the locking position and the second push rod is separated from the carrying unit. When the protrusion moves into a second moving range to be aligned with the driven portion, the protrusion pushes the driven portion so that the locking component is operated to the releasing position and the second push rod is separated from the carrying unit. When the protrusion moves into a third moving range to be misaligned with the driven portion, the locking component is operated to the locking position and the second push rod pushes one of the test strips out of the carrying unit, wherein the second moving range is located between the first moving range and the third moving range.

In an embodiment of invention, the glucose test device includes a second driving unit, wherein the carrying unit has a plurality of first perforated grooves and a plurality of second perforated grooves. The lancets are disposed respectively in the first perforated grooves. The test strips are disposed respectively in the second perforated grooves. The second driving unit is connected to the carrying unit and suitable for driving the carrying unit to rotate so as to align any one of the first perforated grooves with the first push rod and to align any one of the second perforated grooves with the second push rod.

In an embodiment of the invention, when the glucose test device is off, the locking component is located at the locking position. The glucose test device includes a sensing unit. The sensing unit is electrically connected to the control unit and suitable for sensing a state of the carrying unit. When the glucose test device is on and the sensing unit senses that the state of the carrying unit is a predetermined state, the control unit controls the first driving unit to drive the locking component to be operated to the releasing position, wherein the state of the carrying unit includes types of the consumables and a state of use of each consumable.

In an embodiment of the invention, after the first push rod pushes one of the consumables out of the carrying unit, the control unit controls the first driving unit to drive the locking component to be operated to the locking position. The glucose test device has an operation interface suitable for displaying a repeated firing option. After the first push rod pushes one of the consumables out of the carrying unit and the first driving unit drives the locking component to be operated to the locking position, if the repeated firing option is executed, then the control unit controls the first driving unit to drive the locking component to be operated to the releasing position.

In an embodiment of the invention, the glucose test device includes an elastic component, wherein the elastic component is connected between the first push rod and the casing. The first push rod is suitable for resisting an elastic force of the elastic component to move from an initial position to a loading position, and for moving from the loading position toward the carrying unit by the elastic force of the elastic component so as to push one of the consumables out of the carrying unit.

In an embodiment of the invention, the glucose test device includes a stopping component and a pressing component, wherein the stopping component is disposed at the casing and suitable for resisting the elastic force of the elastic component to stop the first push rod at the loading position, and the pressing component is disposed at the casing and suitable for being pressed to drive the stopping component to release the first push rod.

In an embodiment of the invention, the glucose test device includes a pulling component, wherein the pulling component is movably disposed at the casing and has a pulling portion. When the pulling component moves relative to the casing, the pulling component resists the elastic force of the elastic component to pull an end of the first push rod by the pulling portion, so that the first push rod moves from the initial position to the loading position.

In an embodiment of the invention, the control unit has a first switch and a second switch. When the pulling component pulls the first push rod to move from the initial position to the loading position, the pulling component triggers the first switch. When the pressing component is pressed to drive the stopping component to release the first push rod, the pressing component triggers the second switch, wherein after both the first switch and the second switch are triggered, the control unit controls the first driving unit to drive the locking component to be operated to the locking position.

In an embodiment of the invention, the pulling component has a positioning trench, and the locking component has a positioning portion. When the locking component is located at the locking position, the positioning portion extends into the positioning trench to position the pulling component, so as to prevent the pulling component from pulling the first push rod.

In an embodiment of the invention, the pulling component includes an outer casing and an adjusting element. The adjusting element is rotatably disposed at the outer casing and has an adjusting inclined plane. The pulling portion is movably disposed at the outer casing and has a flange. The adjusting element is suitable for rotating to push the flange by the adjusting inclined plane so as to adjust a position of the pulling portion in the outer casing, and a route of the first push rod toward the carrying unit is thus limited.

Based on the above, the glucose test device of the invention uses the carrying unit for containing a plurality of consumables (e.g., lancets and/or test strips) so as to replace the consumables with unused ones by means of the carrying unit for performing blood sampling and testing. Thus, a process of repeatedly installing the consumables is omitted, and further, convenience of operation of the glucose test device is enhanced. In addition, the glucose test device has the locking component disposed therein, and uses the control unit to automatically control the first driving unit to drive the locking component to lock or release the first push rod according to different operation conditions. Accordingly, the user is prevented from firing a lancet by the first push rod in an unexpected operation condition, and further, safety of use of the glucose test device is enhanced.

To make the above features and advantages of the invention more comprehensible, embodiments accompanied with drawings are described in detail as follows.

DESCRIPTION OF DISCLOSED EMBODIMENTS

Figure 1:
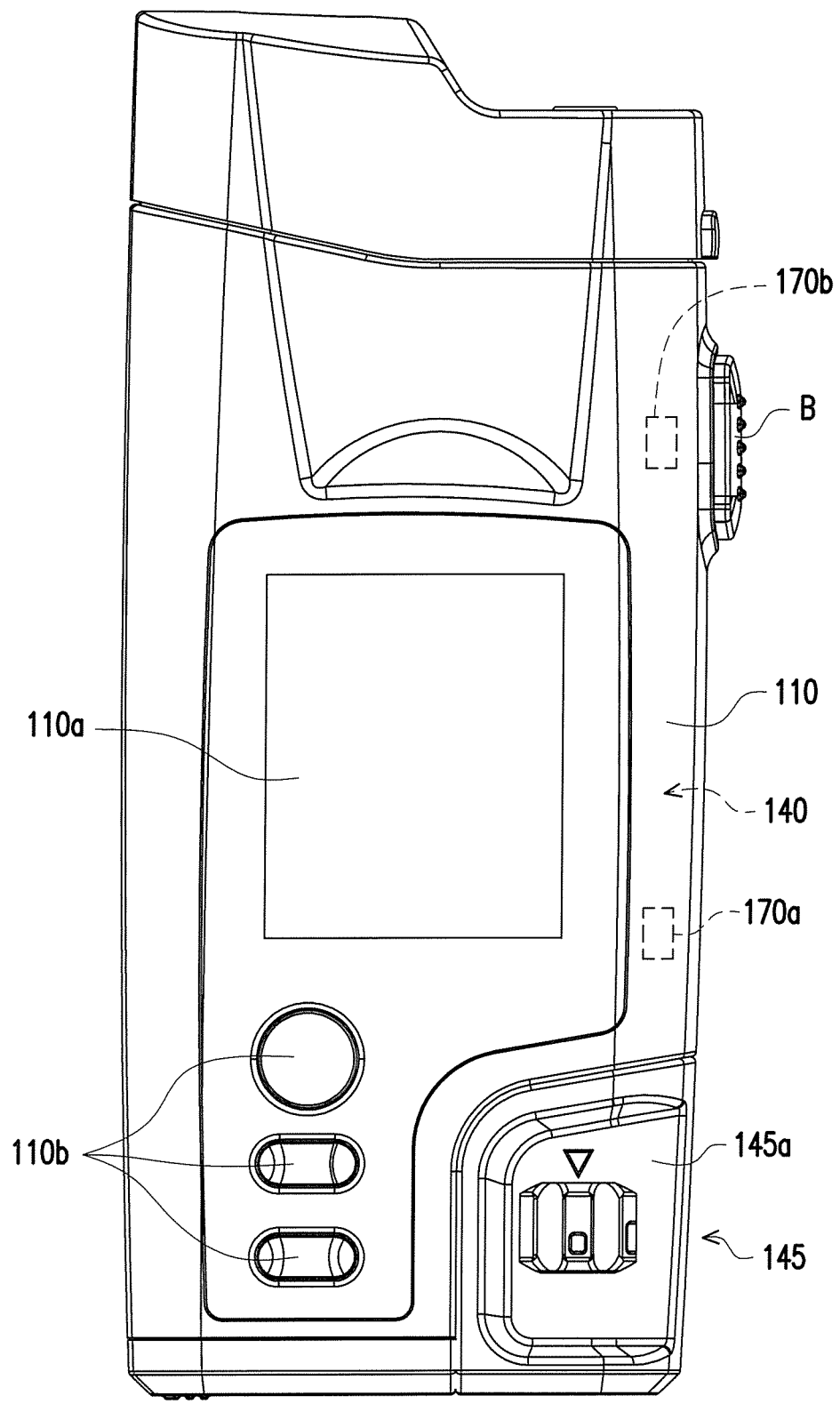
FIG. 1 is a top view of a glucose test device according to an embodiment of the invention.
Figure 2:
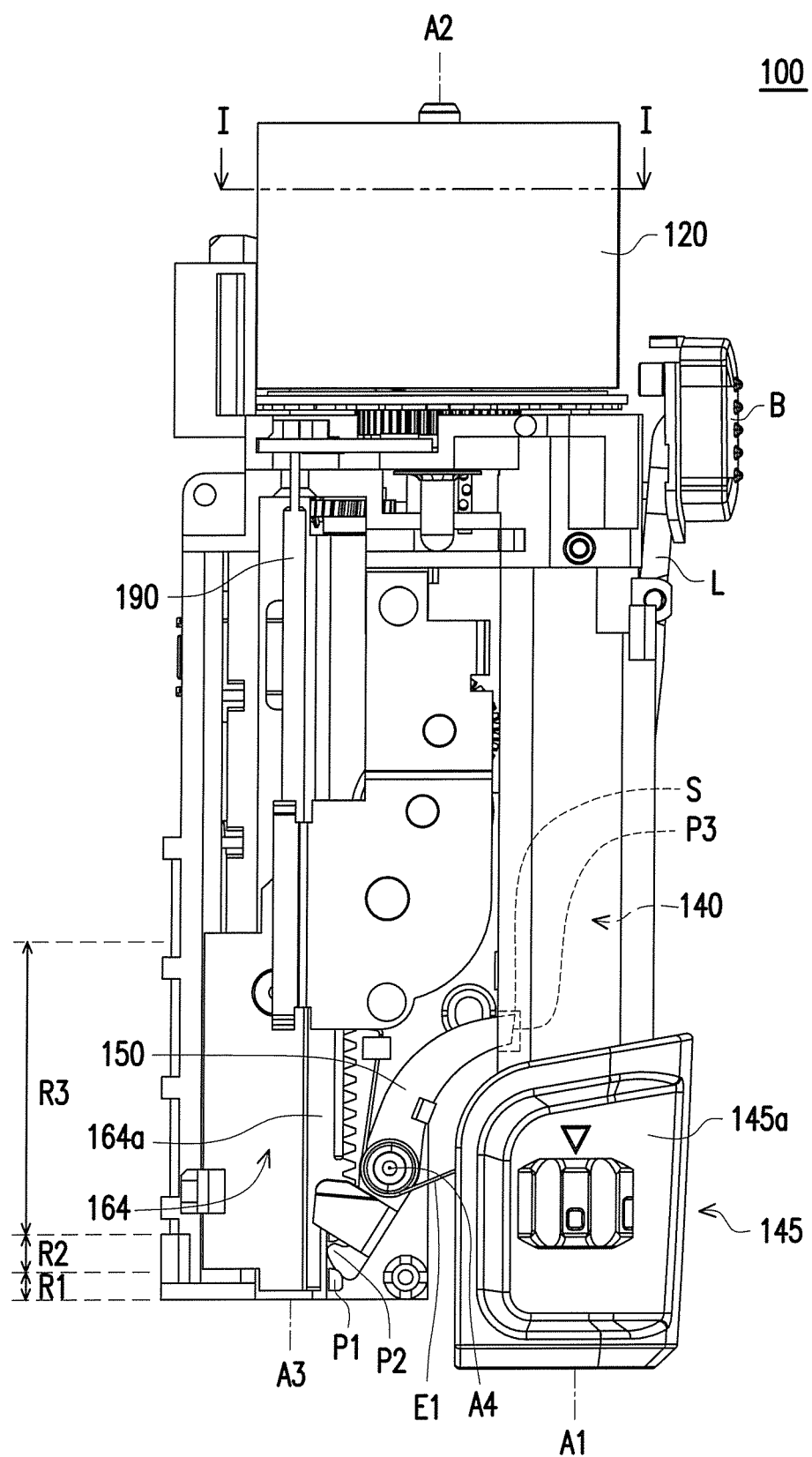
FIG. 2 is a top view of a part of members of the glucose test device in FIG. 1.
Figure 3:
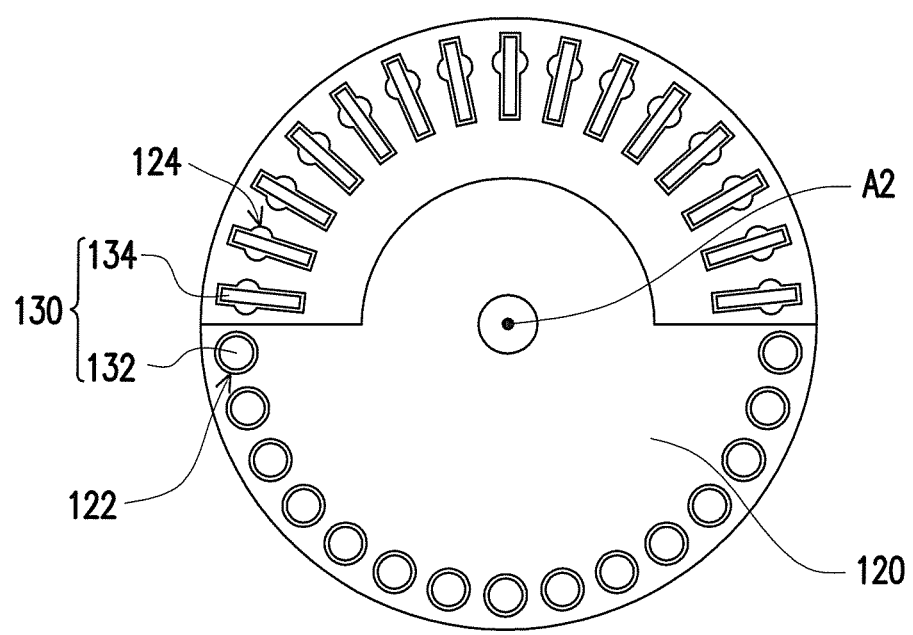
FIG. 3 is a schematic cross-sectional view of the glucose test device taken along line I-I in FIG. 2.
Figure 7A:
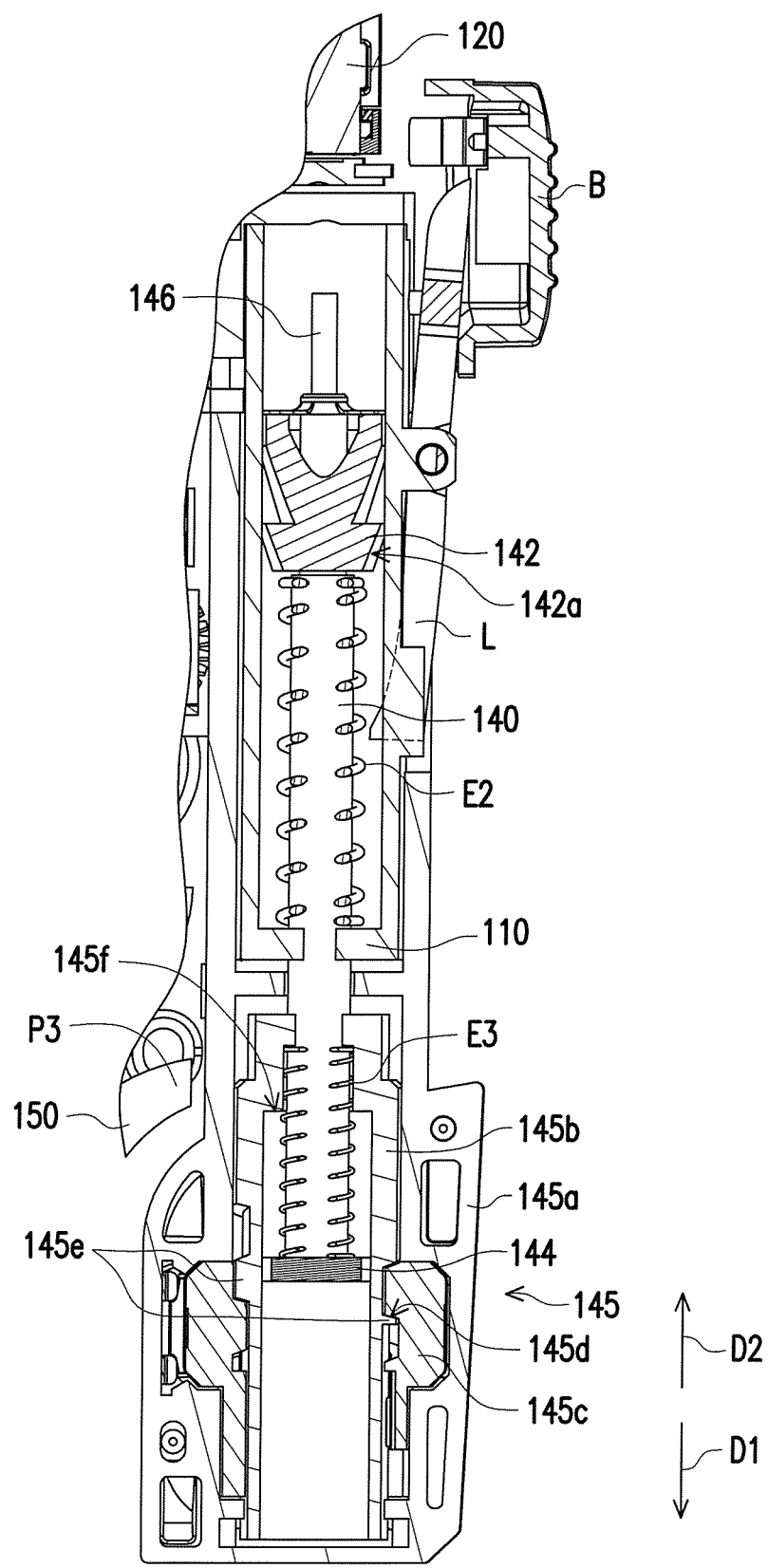
FIG. 7A to FIG. 7D illustrate an operation process of a first push rod in FIG. 2.
Figure 7B:
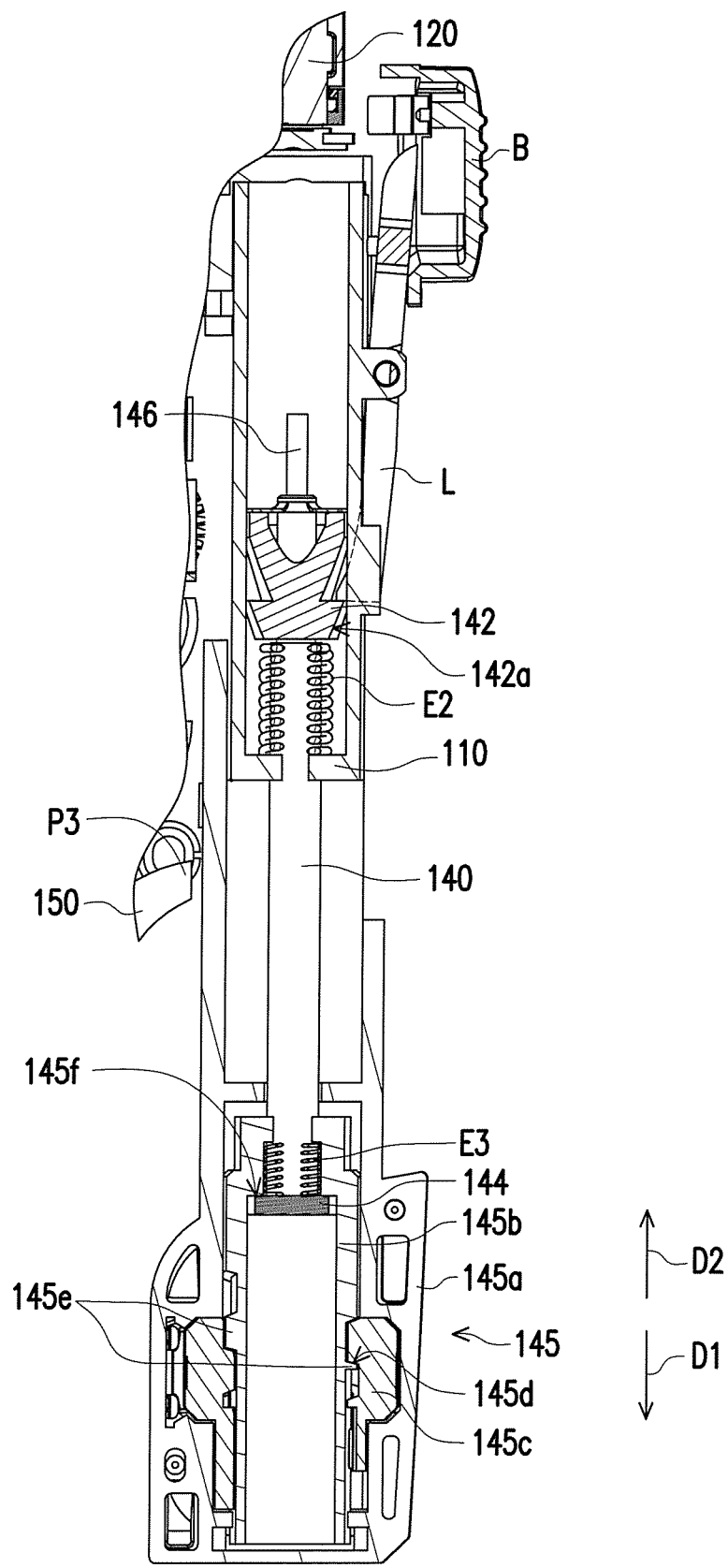
Figure 7C:
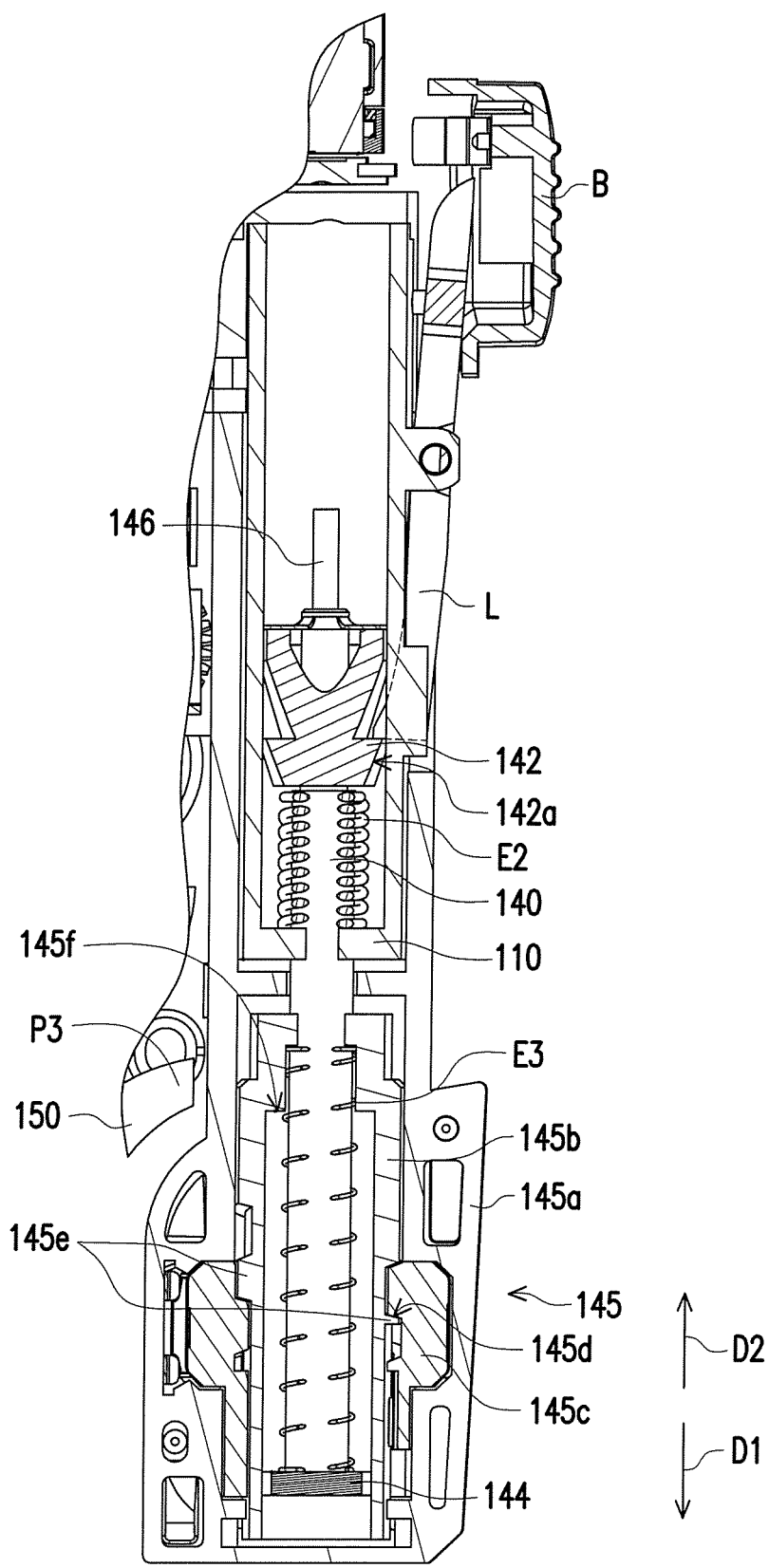

FIG. 1 is a top view of a glucose test device according to an embodiment of the invention. FIG. 2 is a top view of a part of members of the glucose test device in FIG. 1. FIG. 3 is a schematic cross-sectional view of the glucose test device taken along line I-I in FIG. 2. Referring to FIG. 1 to FIG. 3, a glucose test device 100 of the present embodiment includes a casing 110, a carrying unit 120, a plurality of consumables 130, a first push rod 140, a pulling component 145 and a locking component 150. The carrying unit 120 is detachably assembled in the casing 110. The consumables 130 include a plurality of lancets 132 and are disposed in the carrying unit 120. The first push rod 140 is slidably disposed in the casing 110 along a first axis A1 and is aligned with the carrying unit 120, wherein the first push rod 140 is disposed in the casing 110, and a specific structure thereof is illustrated in FIG. 7A. The pulling component 145 is slidably disposed at the casing 110 along the first axis A1.

Figure 4:
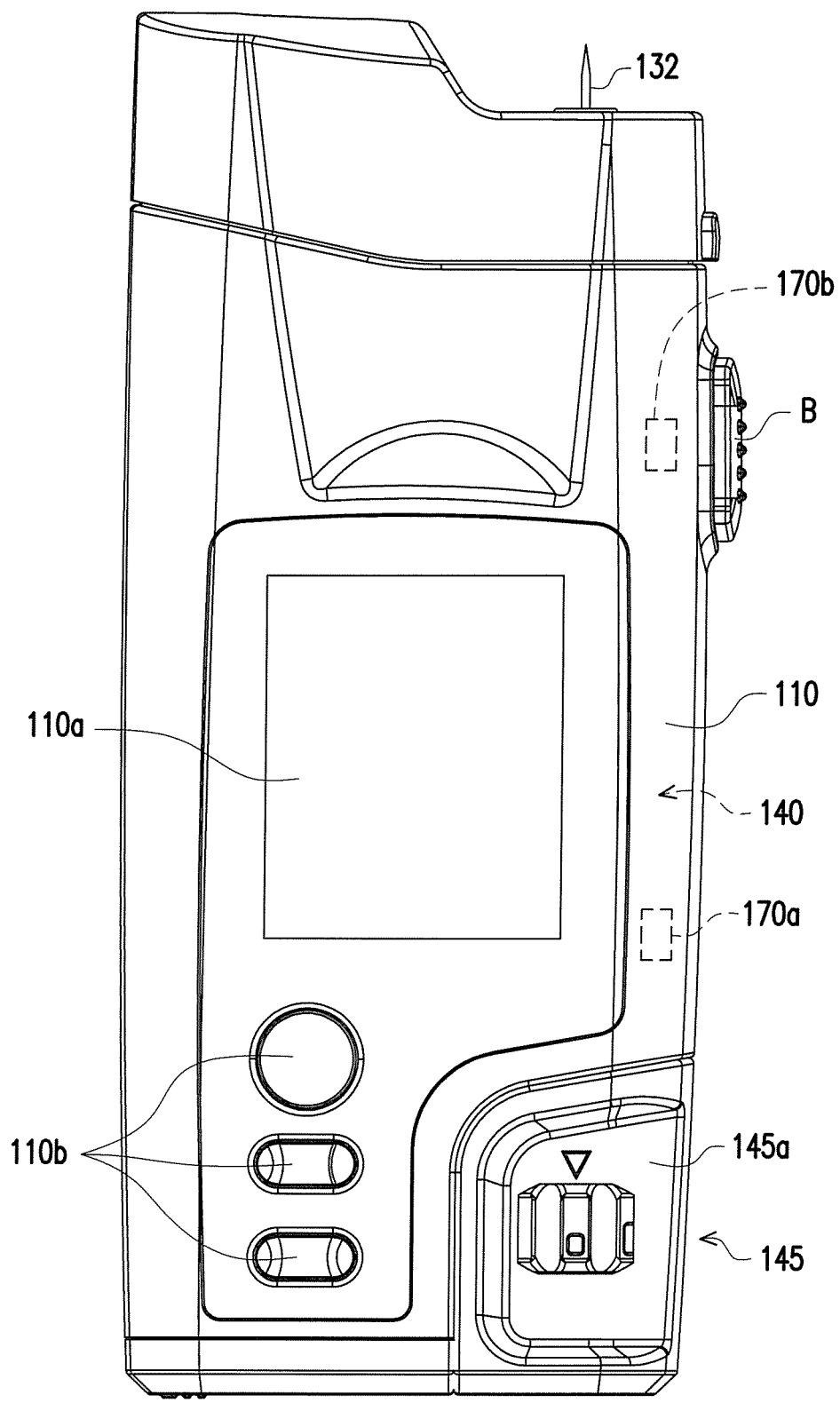
FIG. 4 illustrates that a lancet in FIG. 3 has been pushed outside the casing.

FIG. 4 illustrates that a lancet in FIG. 3 has been pushed outside the casing. The pulling component 145 is suitable for pulling the first push rod 140 along a direction away from the carrying unit 120 to load the first push rod 140. Next, the first push rod 140 is suitable for moving toward the carrying unit 120 so as to push one of the lancets 132 out of the carrying unit 120 as shown in FIG. 4, so that the lancet 132 is fired outside the carrying unit 120 for allowing a user to sample blood. The locking component 150 is movably disposed in the casing 110 and is configured to limit a timing of operation for the first push rod 140. Details thereof are given below with reference to FIG. 5, FIG. 6A and FIG. 6B.

Figure 5:
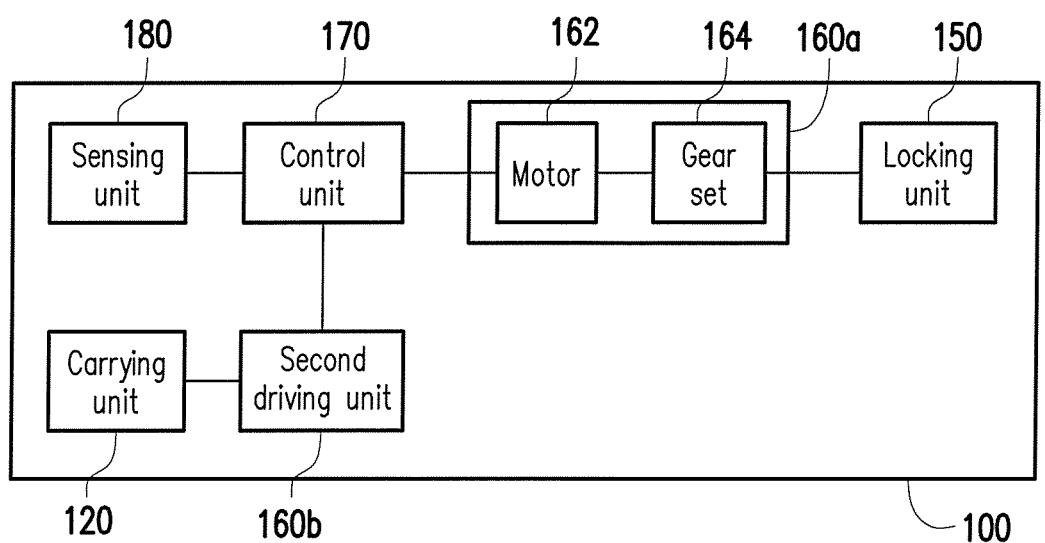
FIG. 5 is a block view of a part of members of the glucose test device in FIG. 1.

FIG. 5 is a block view of a part of members of the glucose test device in FIG. 1. Referring to FIG. 2 and FIG. 5, the glucose test device 100 further includes a first driving unit 160a and a control unit 170. The first driving unit 160a includes a motor 162 and a gear set 164. The gear set 164 is connected between the motor 162 and the locking component 150. The control unit 170 is, e.g., a control circuit board disposed in the casing 110 (illustrated in FIG. 1) and is electrically connected to the first driving unit 160a. For clarity of the drawing, FIG. 2 only illustrates a part of members of the gear set 164 in FIG. 5, such as a rack 164a. The first driving unit 160a may be a driving source of any suitable form and includes suitable types of components and may be disposed at a suitable position in the casing 110. The invention does not impose any limitation on this. In addition, for clarity of the drawing, the control unit 170, a sensing unit 180 and a second driving unit 160b shown in FIG. 5 are not illustrated in FIG. 2.

Figure 6A:
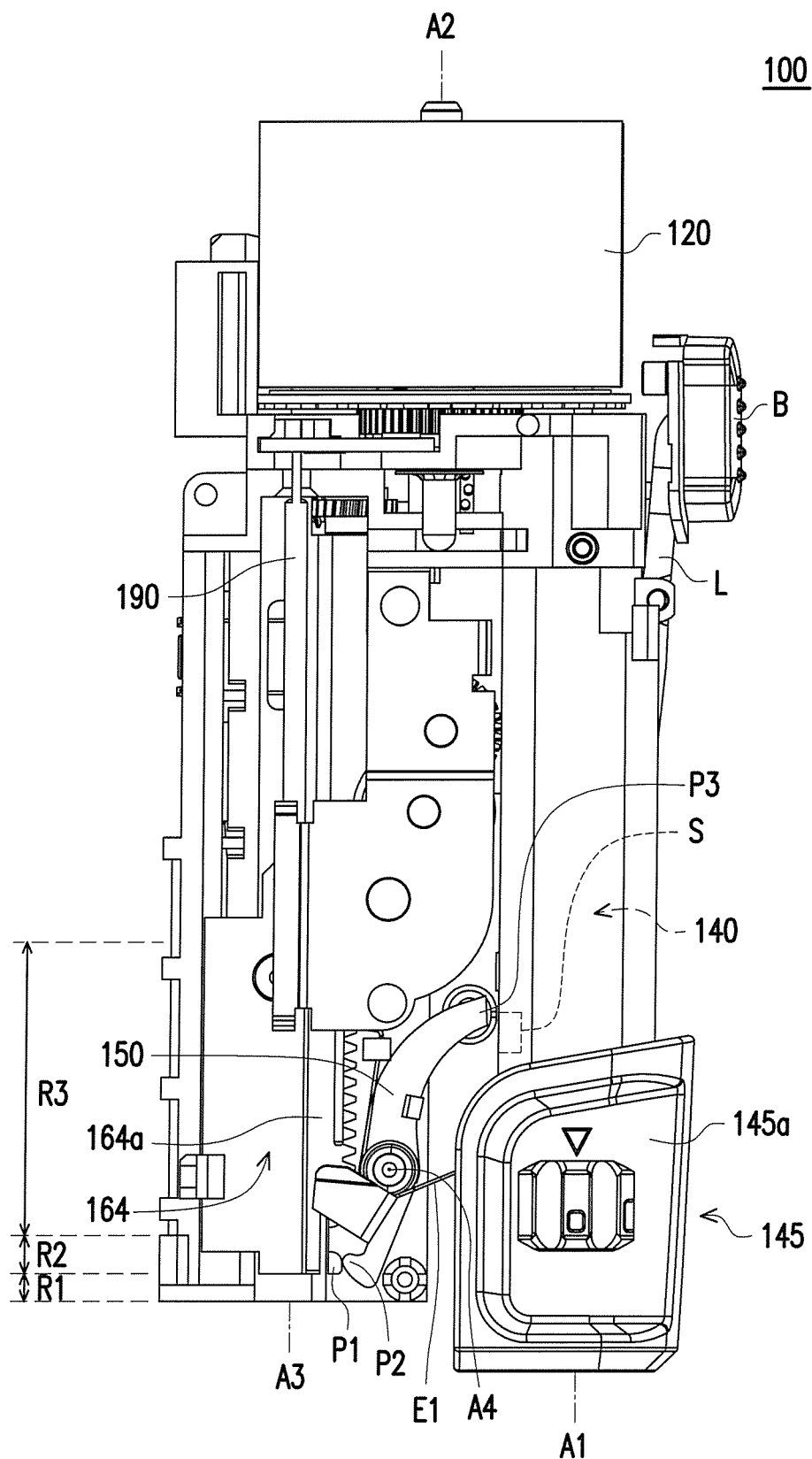
FIG. 6A and FIG. 6B illustrate the glucose test device in FIG. 2 in operation.
Figure 6B:
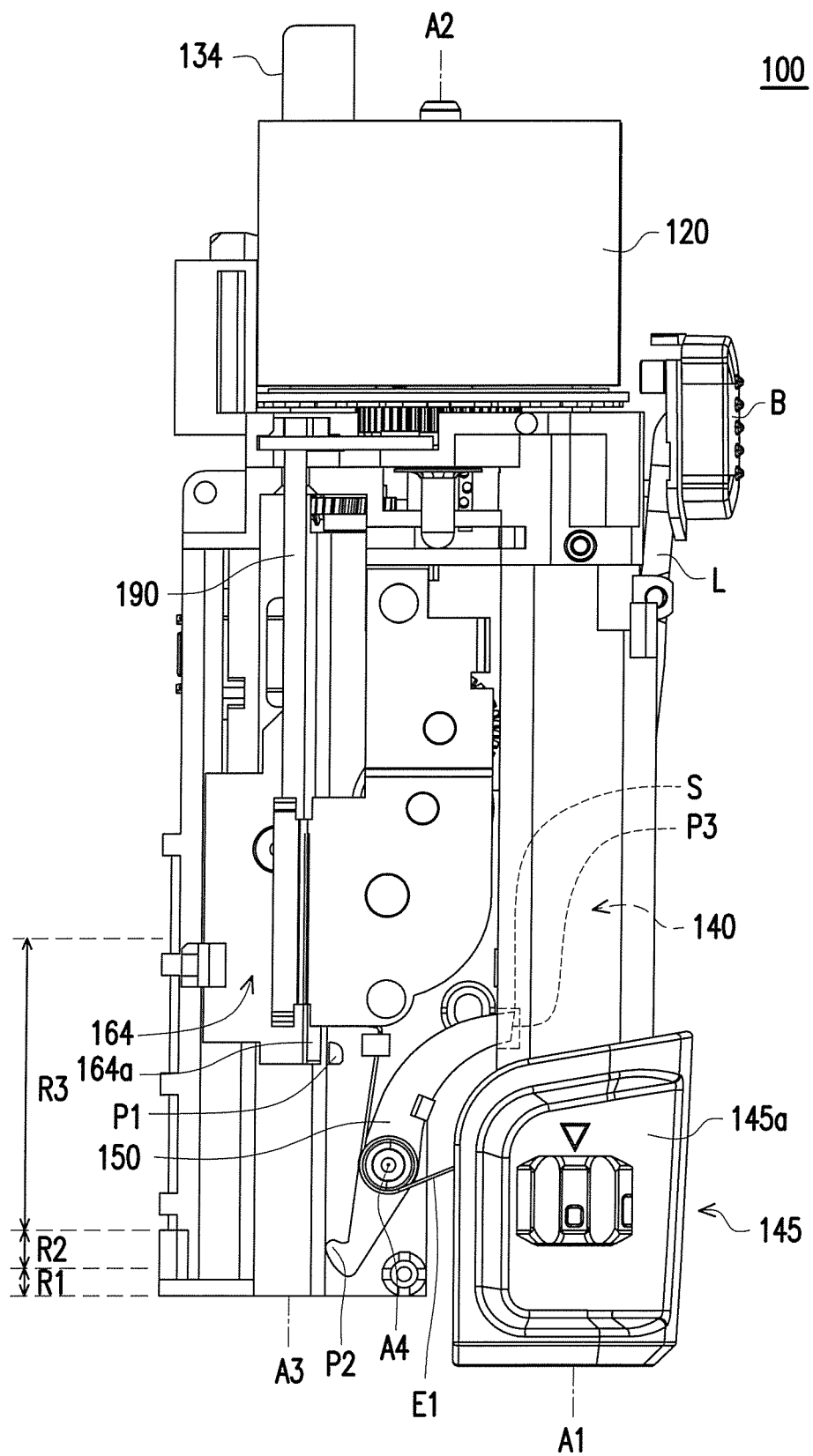

FIG. 6A and FIG. 6B illustrate the glucose test device in FIG. 2 in operation. The control unit 170 shown in FIG. 5 controls the motor 162 of the first driving unit 160a to drive the gear set 164 to operate so that the locking component 150 can be operated to a locking position shown in FIG. 2 or FIG. 6B by driving of the rack 164a of the gear set 164. At this moment, the locking component 150 interferes with the pulling component 145 to prevent the pulling component 145 from pulling the first push rod 140 so as to lock the first push rod 140 from moving along the first axis A1. In addition, the control unit 170 controls the motor 162 of the first driving unit 160a to drive the gear set 164 to operate so that the locking component 150 is operated to a releasing position shown in FIG. 6A by driving of the rack 164a of the gear set 164. At this moment, the locking component 150 does not interfere with the pulling component 145 so as to enable the pulling component 145 to pull the first push rod 140. That is, the first push rod 140 is released.

As mentioned above, the glucose test device 100 has the locking component 150 disposed therein, and uses the control unit 170 to automatically control the first driving unit 160a to drive the locking component 150 to lock or release the first push rod 140 according to different operation conditions. Accordingly, the user is prevented from firing a lancet by the first push rod 140 in an unexpected operation condition, and further, safety of use of the glucose test device 100 is enhanced.

Referring to FIG. 2 and FIG. 3, the carrying unit 120 of the present embodiment is pivotally disposed in the casing 110 (illustrated in FIG. 1) along a second axis A2 parallel to the first axis A1. Moreover, the carrying unit 120 has a plurality of first perforated grooves 122, and the lancets 132 are disposed respectively in the first perforated grooves 122. Following the above, as shown in FIG. 5, the glucose test device 100 of the present embodiment includes the second driving unit 160b. The second driving unit 160b is connected to the carrying unit 120 and suitable for driving the carrying unit 120 to rotate around the second axis A2 so as to align any one of the first perforated grooves 122 with the first push rod 140. Accordingly, the carrying unit 120 is driven by the second driving unit 160b, and by the rotation of the carrying unit 120, the lancet 132 is replaced with an unused lancet 132 for performing blood sampling. A process of repeatedly installing the lancet 132 is omitted, and further, convenience of operation of the glucose test device 100 is enhanced. Similar to the first driving unit 160a, the second driving unit 160b includes, e.g., a motor and a gear set. However, the invention is not limited thereto. The second driving unit 160b may be a driving source of any suitable form and includes suitable types of components and may be disposed at a suitable position in the casing 110. In other embodiments, the first driving unit 160a may be connected to the carrying unit 120 and the first driving unit 160a may be used to drive the carrying unit 120 to rotate around the second axis A2. The invention does not impose any limitation on this.

Referring to FIG. 3, the consumables 130 further include a plurality of test strips 134. The carrying unit 120 further has a plurality of second perforated grooves 124. The test strips 134 are disposed respectively in the second perforated grooves 124. Following the above, referring to FIG. 2, the glucose test device 100 of the present embodiment further includes a second push rod 190. The second push rod 190 is slidably disposed in the casing 110 (illustrated in FIG. 1) along a third axis A3 parallel to the first axis A1 and the second axis A2 and is aligned with the carrying unit 120. Moreover, the second push rod 190 is connected to the first driving unit 160a shown in FIG. 5. After the lancet 132 is instantly fired outside the carrying unit 120 by the first push rod 140 (as shown in FIG. 4) as mentioned above and the user performs blood sampling, the lancet 132 is instantly restored into the carrying unit 120. Moreover, the control unit 170 controls the first driving unit 160a to drive the second push rod 190 to move toward the carrying unit 120 so as to push one of the test strips 134 out of the carrying unit 120 (as shown in FIG. 6B), enabling the user to easily place the sampled blood on the test strip 134 for performing glucose testing.

It is noted that the first driving unit 160a of the present embodiment is not only configured to drive the second push rod 190 to operate to push the test strip 134 as mentioned above, but also configured to drive the locking component 150 to operate to lock or release the first push rod 140 as mentioned previously. In other words, the second push rod 190 and the locking component 150 share the same driving source (i.e., the first driving unit 160a), thus saving the manufacturing cost of the glucose test device 100 and disposition space therein.

Furthermore, when the second driving unit 160b shown in FIG. 5 drives the carrying unit 120 to rotate to align any one of the unused lancets 132 in the first perforated grooves 122 with the first push rod 140, any one of unused test strips 134 in the second perforated grooves 124 is also aligned with the second push rod 190 with the rotation of the carrying unit 120. Accordingly, by the rotation of the carrying unit 120, the test strip 134 is replaced with the unused test strip 134 for performing blood testing. A process of repeatedly installing the test strip 134 is omitted, and further, convenience of operation of the glucose test device 100 is enhanced.

The glucose test device 100 of the present embodiment further includes the sensing unit 180 (illustrated in FIG. 5). The sensing unit 180 is electrically connected to the control unit 170 and suitable for sensing a state of the carrying unit 120, so that the control unit 170 can control operation of the glucose test device 100 accordingly. Details thereof will be described later. The state of the carrying unit 120 includes, e.g., types of the lancets 132 (illustrated in FIG. 3) and a state of use of each lancet 132. The sensing unit 180, for example, senses a barcode on the carrying unit 120 and thereby determines the types of the lancets 132 in the carrying unit 120, and senses whether a certain position on a film (not shown) on an outer surface of the carrying unit 120 that covers the lancets 132 has been penetrated by a lancet 132, and thereby determines whether the corresponding lancet 132 has been used. The sensing unit 180 may be a sensing element of any suitable form and is disposed at a suitable position in the casing 110 and performs sensing in any suitable way. The invention does not impose any limitation on this.

An operation process of the glucose test device 100 of the present embodiment is specifically described below.

When the glucose test device 100 is off, the locking component 150 is located at the locking position to lock the first push rod 140 as shown in FIG. 2 so as to prevent the user from erroneously operating the first push rod 140 and firing a used lancet 132 (illustrated in FIG. 3) in the carrying unit 120 while the glucose test device 100 is off, for the purpose of preventing infection.

When the glucose test device 100 is turned on by the user, the sensing unit 180 senses the state of the carrying unit 120. If the sensing unit 180 senses that the state of the carrying unit 120 is a predetermined state (e.g., the lancets 132 are of a predetermined type and there are unused lancets 132), then the control unit 170 controls the second driving unit 160b shown in FIG. 5 to drive the carrying unit 120 to rotate so as to align an unused lancet 132 with the first push rod 140 shown in FIG. 2. Moreover, the control unit 170 controls the first driving unit 160a to drive the locking component 150 to be operated to the releasing position to release the first push rod 140 as shown in FIG. 6A. As mentioned above, the first push rod 140 is released after the sensing unit 180 senses that the state of the carrying unit 120 is the predetermined state. Thus, the user is prevented from erroneously operating the first push rod 140 while the carrying unit 120 is absent or the sensing unit 180 is still in operation and thus causing damage to the glucose test device 100.

After the first driving unit 160a drives the locking component 150 to be operated to the releasing position to release the first push rod 140 as shown in FIG. 6A, the user drives the first push rod 140 to operate, so that the first push rod 140 pushes one of the lancets 132 shown in FIG. 3 outside the carrying unit 120 as shown in FIG. 4 for allowing the user to sample blood. Next, the lancet 132 is restored into the carrying unit 120, and the control unit 170 controls the first driving unit 160a to drive the second push rod 190 to push one of the test strips 134 shown in FIG. 3 out of the carrying unit 120 as shown in FIG. 6B, enabling the user to easily place the blood on the test strip 134 for performing glucose testing. When the first driving unit 160a drives the second push rod 190 by the gear set 164 thereof to push the test strip 134 out of the carrying unit 120, the first driving unit 160a synchronously drives the locking component 150 by the rack 164a of the gear set 164 thereof to be operated to the locking position as shown in FIG. 6B to again interfere with the pulling component 145 so as to lock the first push rod 140. Thus, the user is prevented from erroneously operating the pulling component 145 to drive the first push rod 140 to repeat firing of a used lancet 132, and thereby infection is prevented. After the user places the blood on the test strip 134 and the glucose test device 100 completes detection of the test strip 134, the glucose test device 100 automatically causes the test strip 134 to detach from the carrying unit 120. Moreover, the first driving unit 160a drives the second push rod 190 to pass the position shown in FIG. 6A instantly from the position shown in FIG. 6B and then to restore to the position shown in FIG. 2, and synchronously drives the locking component 150 to pass the state shown in FIG. 6A instantly from the state shown in FIG. 6B and then to restore to the state shown in FIG. 2, so as to allow the user to perform another blood sampling and testing in accordance with the above process shown in FIG. 2, FIG. 6A to FIG. 6B.

In detail, the rack 164a of the first driving unit 160a of the present embodiment has a protrusion P1 as shown in FIG. 2. The second push rod 190 and the rack 164a are fixed to each other so that the protrusion P1 moves synchronously with the second push rod 190. The locking component 150 has a driven portion P2. When the protrusion P1 moves into a first moving range R1 to be misaligned with the driven portion P2 as shown in FIG. 2, the locking component 150 is located at the locking position to lock the first push rod 140. Moreover, at this moment, the second push rod 190 is separated from the carrying unit 120 and has not yet pushed the test strip 134 (illustrated in FIG. 3) in the carrying unit 120. When the protrusion P1 moves into a second moving range R2 to be aligned with the driven portion P2 as shown in FIG. 6A, the protrusion P1 pushes the driven portion P2 so that the locking component 150 is operated to the releasing position to release the first push rod 140. Moreover, at this moment, the second push rod 190 is separated from the carrying unit 120 and has not yet pushed the test strip 134 (illustrated in FIG. 3) in the carrying unit 120. When the protrusion P1 moves into a third moving range R3 to be misaligned with the driven portion P2 as shown in FIG. 6B, the locking component 150 is operated to the locking position to lock the first push rod 140. Moreover, at this moment, with the operation of the first driving unit 160a, the second push rod 190 pushes one of the test strips 134 out of the carrying unit 120. The second moving range R2 is located between the first moving range R1 and the third moving range R3.

Referring to FIG. 1, the glucose test device 100 of the present embodiment has an operation interface. The operation interface includes, e.g., a display surface 110a and buttons 110b, for allowing the user to operate. For example, after the first push rod 140 pushes one of the lancets 132 out of the carrying unit 120 as shown in FIG. 4 and the first driving unit 160a (illustrated in FIG. 5) drives the locking component 150 to be operated to the locking position (as shown in FIG. 6B), the operation interface displays a repeated firing option on the display surface 110a thereof. If blood has failed to be sampled, then the user executes the repeated firing option by the buttons 110b. At this moment, the test strip 134 is still located at the position as shown in FIG. 6B, and the control unit 170 (illustrated in FIG. 5) controls the first driving unit 160a to drive the locking component 150 to be operated to the releasing position to release the first push rod 140 as shown in FIG. 6A, so that the user, when having failed to sample the blood, may sample the blood by re-firing the same lancet 132 by the first push rod 140. When the operation interface displays the repeated firing option on the display surface 110a thereof as mentioned above, the display surface 110a synchronously displays a warning text to tell the user the risk of infection due to repeated firing of the lancet 132, and thereby the safety of use of the glucose test device 100 is enhanced.

After the user executes the repeated firing option to re-fire the same lancet 132 by the first push rod 140 and samples the blood as mentioned above, the user places the blood on the test strip 134 located at the position as shown in FIG. 6B for ease of the glucose testing. Moreover, the first driving unit 160a drives the locking component 150 by the rack 164a of the gear set 164 thereof to be operated to the locking position as shown in FIG. 6B to again interfere with the pulling component 145 so as to lock the first push rod 140. Thus, the user is prevented from erroneously operating the pulling component 145 to drive the first push rod 140 to repeat firing the used lancet 132. After the user places the blood on the test strip 134, the first driving unit 160a drives the second push rod 190 to pass the position shown in FIG. 6A from the position shown in FIG. 6B and then to restore to the position shown in FIG. 2, and synchronously drives the locking component 150 to pass the state shown in FIG. 6A from the state shown in FIG. 6B and then to restore to the state shown in FIG. 2.

A specific configuration of the locking component 150 of the present embodiment is described below. Referring to FIG. 2, in the present embodiment, the locking component 150 is pivotally disposed at the casing 110 along a fourth axis A4 and suitable for rotating along the fourth axis A4 to be operated to the locking position shown in FIG. 2 and FIG. 6B or the releasing position shown in FIG. 6A, wherein the fourth axis A4 is, e.g., perpendicular to the first axis A1. The pulling component 145 of the present embodiment has a positioning trench S, and the locking component 150 has a positioning portion P3. When the locking component 150 is located at the locking position as shown in FIG. 2 and FIG. 6B, the positioning portion P3 extends into the positioning trench S to lock the pulling component 145, so as to prevent the pulling component 145 from pulling the first push rod 140. In addition, the glucose test device 100 includes an elastic component E1. The elastic component E1 is, e.g., a torsion spring, and is connected between the locking component 150 and the casing 110. The locking component 150 is suitable for resisting an elastic force of the elastic component E1 to be operated from the locking position shown in FIG. 2 and FIG. 6B to the releasing position shown in FIG. 6A. Moreover, the locking component 150 is suitable for being restored from the releasing position shown in FIG. 6A to the locking position shown in FIG. 2 and FIG. 6B by the elastic force of the elastic component E1. In other embodiments, the locking component 150 may be movably disposed at the casing 110 in other suitable ways, and may lock the first push rod 140 by other suitable structures. The invention does not impose any limitation on this.

A specific operation manner of the first push rod 140 of the present embodiment is described with reference to drawings.

Figure 7D:
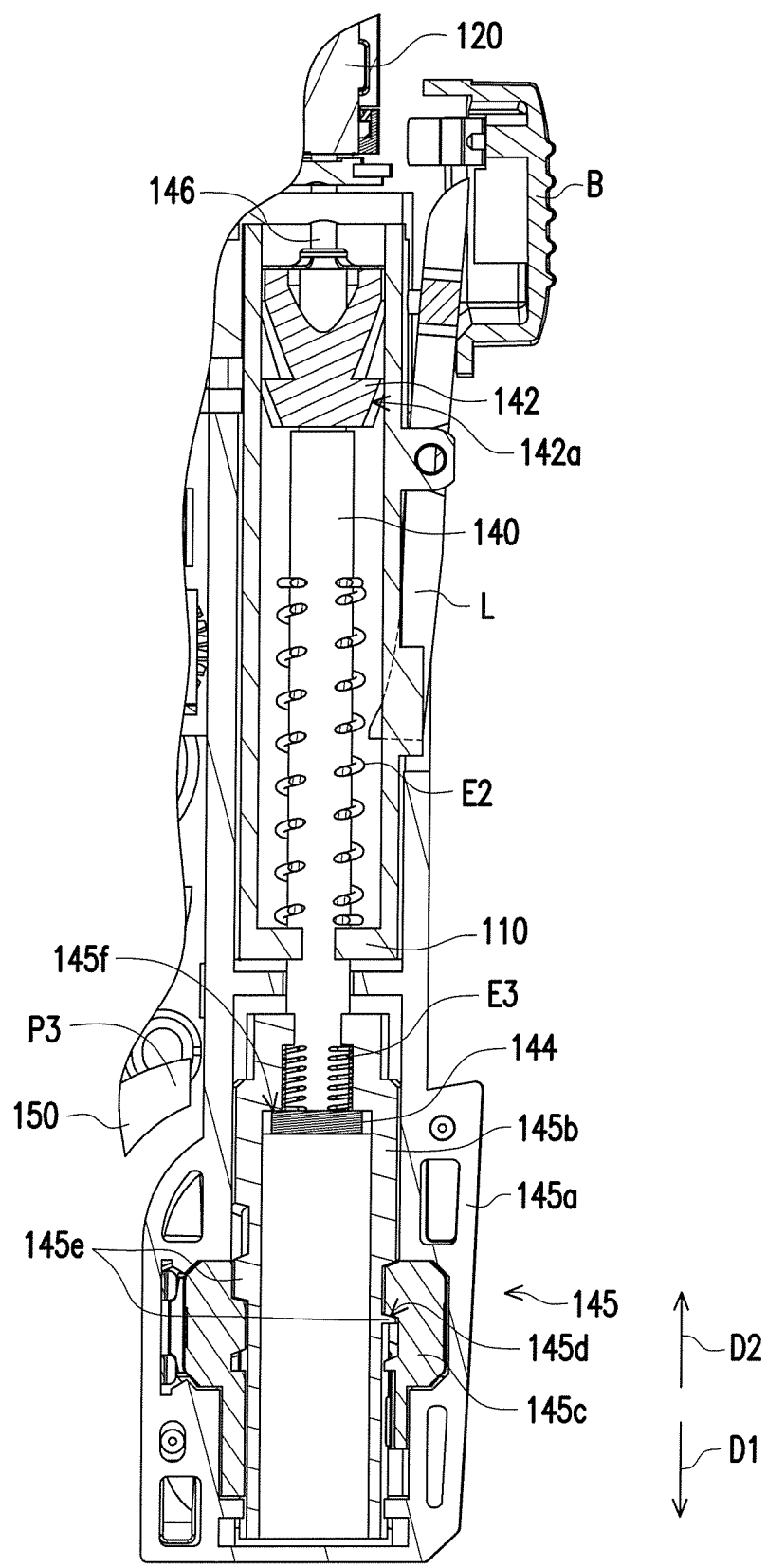

FIG. 7A to FIG. 7D illustrate an operation process of the first push rod 140 in FIG. 2. Referring to FIG. 7A, the glucose test device 100 of the present embodiment includes an elastic component E2, a stopping component L and a pressing component B. The elastic component E2 is, e.g., a compression spring, and is connected between the first push rod 140 and the casing 110. The stopping component L and the pressing component B are disposed at the casing 110. The first push rod 140 has a flange 142, and the flange 142 has a guiding inclined plane 142a. The pulling component 145 includes an outer casing 145a and a pulling portion 145b disposed in the outer casing 145a. The user pulls the outer casing 145a so that the pulling component 145 resists an elastic force of the elastic component E2 to pull an end 144 of the first push rod 140 by the pulling portion 145b in the outer casing 145a along a direction D1 away from the carrying unit 120. Thus, the first push rod 140 resists the elastic force of the elastic component E2 to move from an initial position shown in FIG. 7A to a loading position shown in FIG. 7B along the direction D1. During this process, the first push rod 140 crosses over the stopping component L by guidance of the guiding inclined plane 142a. When the user releases the pulling component 145, the pulling component 145 is restored to the position shown in FIG. 7C along a direction D2 opposite the direction D1 by an elastic force of an elastic component E3 (at this moment the first push rod 140 remains at the loading position). The elastic component E3 is, e.g., a compression spring, and is connected between the first push rod 140 and the pulling portion 145b. In the state shown in FIG. 7C, the stopping component L leans against the flange 142 and resists the elastic force of the elastic component E2 to stop the first push rod 140 at the loading position. Next, the user presses the pressing component B to drive the stopping component L to release the first push rod 140. At this moment, the first push rod 140 moves from the loading position shown in FIG. 7B toward the carrying unit 120 along the direction D2 by the elastic force of the elastic component E2, as shown in FIG. 7D. Thus, one of the lancets 132 is pushed out of the carrying unit 120 by a front end 146 (denoted in FIG. 7A to FIG. 7C) of the first push rod 140, as shown in FIG. 4.

Furthermore, in the present embodiment, the control unit 170 shown in FIG. 3 has a first switch 170a (illustrated in FIG. 1 and FIG. 4) and a second switch 170b illustrated in FIG. 1 and FIG. 4). When the first push rod 140 moves from the initial position shown in FIG. 7A to the loading position shown in FIG. 7B by the user's pulling the pulling component 145 and the pulling component 145 is restored from the position shown in FIG. 7B to the position shown in FIG. 7C by the elastic force of the elastic component E3, the pulling component 145 will trigger the first switch 170a. After the pulling component 145 triggers the first switch 170a, the control unit 170 controls the display surface 110a to display a hint text to tell the user that the first push rod 140 is in a loading state ready for the firing. Next, when the pressing component B is pressed by the user to drive the stopping component L to release the first push rod 140 so as to fire the lancet 132 by the first push rod 140, the pressing component B will trigger the second switch 170b. After both the first switch 170a and the second switch 170b are triggered, the control unit 170 determines that the first push rod 140 has completed the firing of the lancet 132, and controls the first driving unit 160a to drive the locking component 150 to be operated to the locking position to lock the first push rod 140 as shown in FIG. 6B. At this moment, the first driving unit 160a synchronously drives the second push rod 190 by the gear set 164 thereof to push the test strip 134 out of the carrying unit 120 (as shown in FIG. 6B).

Figure 7E:
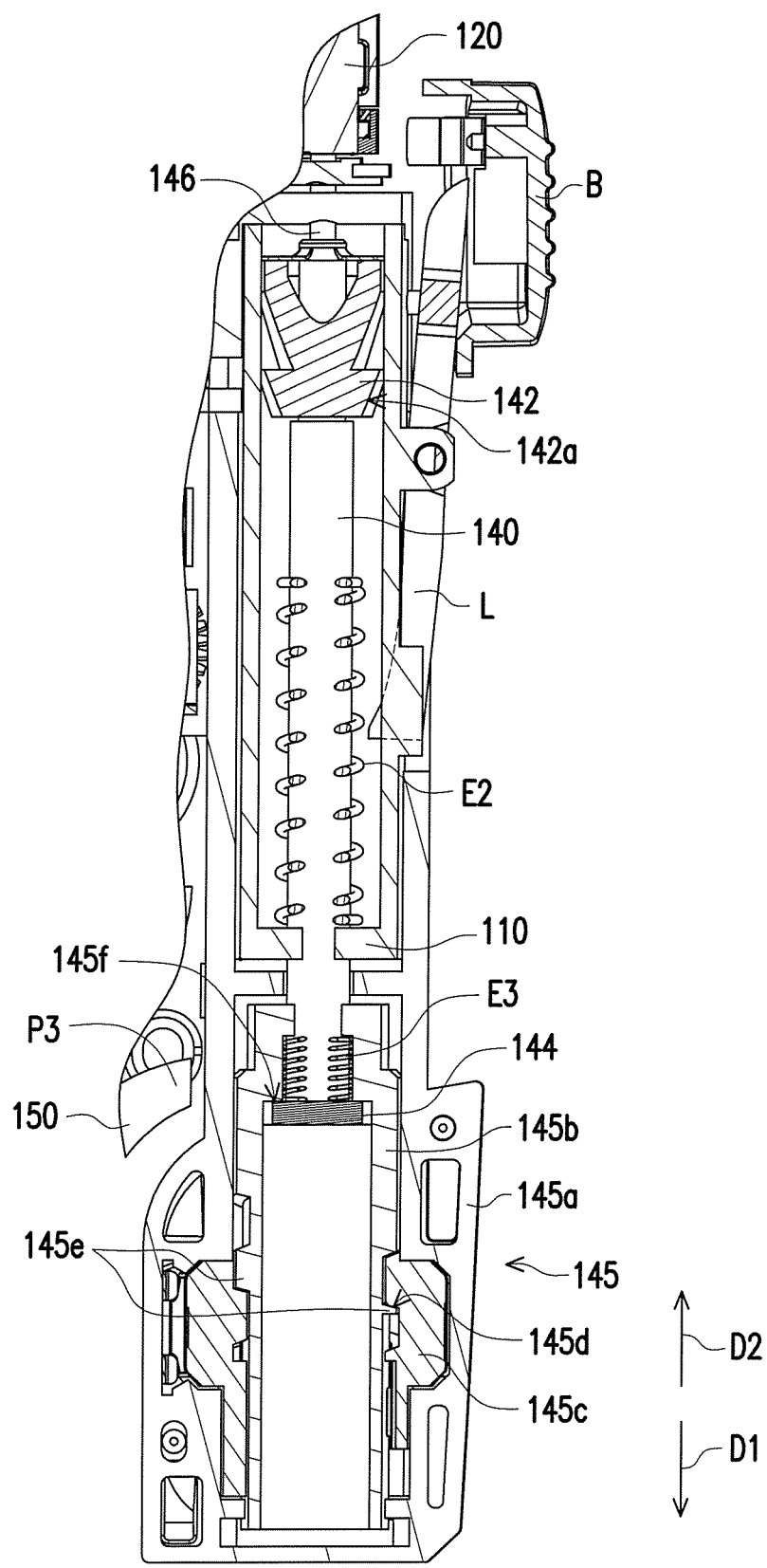
FIG. 7E illustrates that positions of a pulling portion and the first push rod in FIG. 7D have been adjusted.

FIG. 7E illustrates that positions of the pulling portion and the first push rod in FIG. 7D have been adjusted. As shown in FIG. 7A, the pulling component 145 of the present embodiment includes an adjusting element 145c. The adjusting element 145c is, e.g., a knob, rotatably disposed at the outer casing 145a and having an adjusting inclined plane 145d, wherein the adjusting element 145c is disposed at the outer casing 145a by, e.g., screwing, and the adjusting inclined plane 145d is a surface of an internal thread of the adjusting element 145c. The pulling portion 145b has at least one flange 145e. The adjusting element 145c is suitable for rotating by operation of the user so as to push the flange 145e of the pulling portion 145b by the adjusting inclined plane 145d. Accordingly, as shown in FIG. 7E, a position of a stopping structure 145f of the pulling portion 145b in the outer casing 145a is adjusted along the direction D2. Further, by the stopping of the stopping structure 145f performed on the end 144 of the first push rod 140, a route of the first push rod 140 toward the carrying unit 120 is limited. Thus, a length of the lancet protruding from the casing 110 is changed according to user's needs. In other embodiments, the position of the stopping structure 145*f* of the pulling portion 145*b* in the outer casing 145*a* may be adjusted along the direction D1 by the adjusting element 145*c*. The invention does not impose any limitation on this.

Figure 8A:
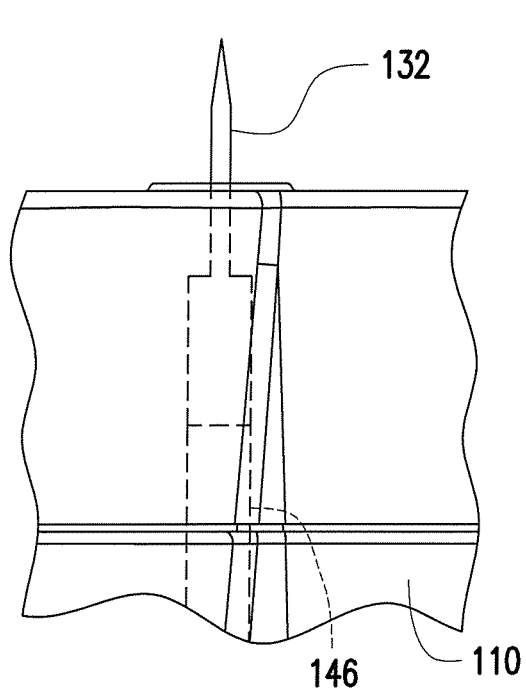
FIG. 8A illustrates that the lancet in FIG. 3 is fired by the pulling portion and the first push rod in FIG. 7D.
Figure 8B:
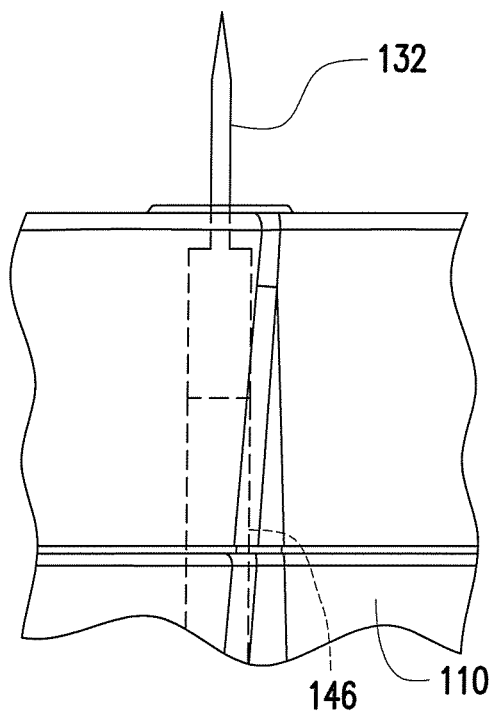
FIG. 8B illustrates that the lancet in FIG. 3 is fired by the pulling portion and the first push rod with their positions adjusted in FIG. 7E.

FIG. 8A illustrates that the lancet in FIG. 3 is fired by the pulling portion and the first push rod in FIG. 7D. FIG. 8B illustrates that the lancet in FIG. 3 is fired by the pulling portion and the first push rod with their positions adjusted as shown in FIG. 7E. By means of adjusting the position of the stopping structure 145*f* of the pulling portion 145*b* through the adjusting element 145*c* to limit the route of the first push rod 140 toward the carrying unit 120 as mentioned above, a distance the first push rod 140 pushes the lancet 132 can be changed while the first push rod 140 fires the lancet 132, so that the length of the lancet 132 protruding out of the casing 110 varies as shown between FIG. 8A and FIG. 8B, thereby satisfying various user's needs.

In addition, when the glucose test device 100 of another embodiment uses a carrying unit that carries only test strips and no lancets, since there is no need to fire a lancet, the locking component 150 remains at the locking position and in a state of locking the first push rod 140. When the glucose test device 100 of still another embodiment uses a carrying unit that carries only lancets and no test strips, since there is no need to push a test strip by the second push rod 190, the first driving unit 160*a* does not drive the second push rod 190 to be operated toward the carrying unit 120 but only performs the operations as shown in FIG. 2 and FIG. 6A in a cyclic manner. Following the above, the glucose test device 100 senses the barcode on the carrying unit, thereby determining the types of the consumables in the carrying unit, such as a first type of carrying unit exemplified by the carrying unit 120 carrying both the lancets 132 and the test strips 134 as shown in FIG. 3, or a second type of carrying unit exemplified by the carrying unit carrying only lancets, or a third type of carrying unit exemplified by the carrying unit carrying only test strips. According to the first type of carrying unit, the second type of carrying unit and the third type of carrying unit, different operation manners are performed as mentioned above. In other words, the glucose test device 100 of the invention may apply three different types of carrying units through a cooperation of the control unit 170 and the locking component 150. In addition, the glucose test device 100 of the invention may only apply one of the first type of carrying unit, the second type of carrying unit and the third type of carrying unit and performs a corresponding operation manner, or may only apply two of the first type of carrying unit, the second type of carrying unit and the third type of carrying unit and performs corresponding operation manners respectively. The invention does not impose any limitation on this.

Figure 9:
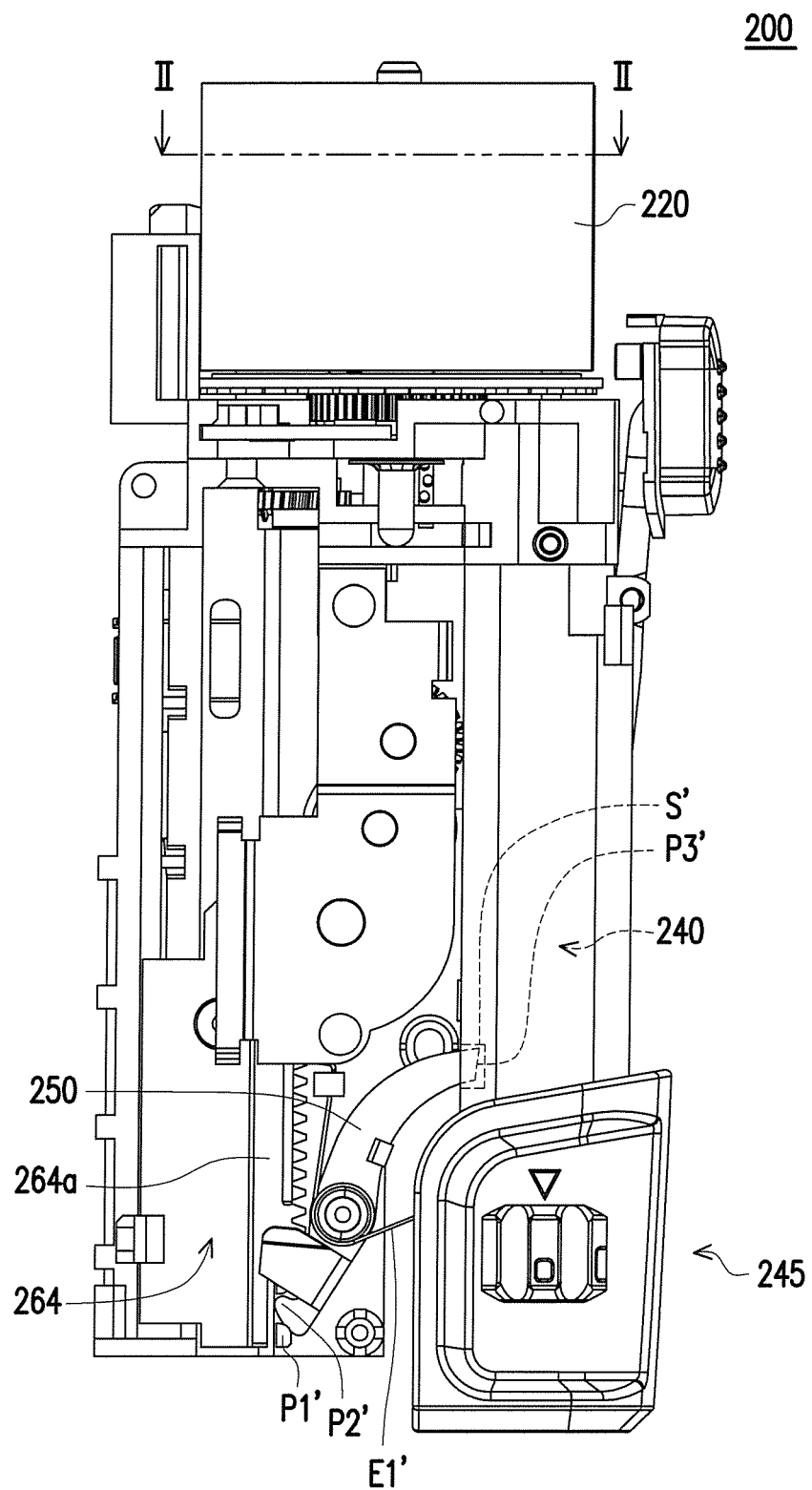
FIG. 9 is a top view of a part of members of a glucose test device according to another embodiment of the invention.
Figure 10:
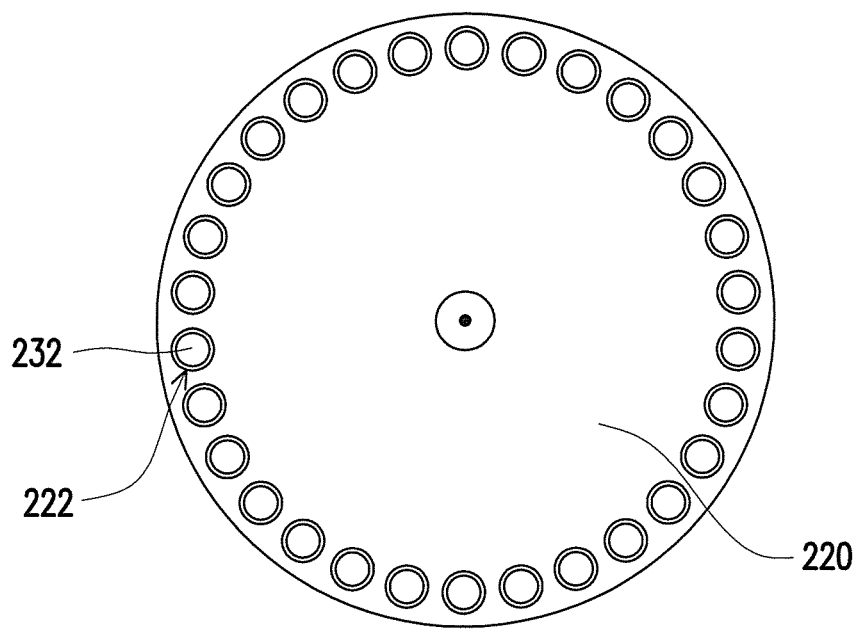
FIG. 10 is a schematic cross-sectional view of the glucose test device taken along line II-II in FIG. 9.

FIG. 9 is a top view of a part of members of a glucose test device according to another embodiment of the invention. FIG. 10 is a schematic cross-sectional view of the glucose test device taken along line II-II in FIG. 9. In a glucose test device 200 shown in FIG. 9 and FIG. 10, a carrying unit 220, first perforated grooves 222, lancets 232, a gear set 264 of a first driving unit, a rack 264*a*, a protrusion P1', a first push rod 240, a pulling component 245, a positioning trench S', a locking component 250, a driven portion P2', a positioning portion P3' and an elastic component E1' are disposed and operate in similar manners to the carrying unit 120, the first perforated grooves 122, the lancets 132, the gear set 164 of the first driving unit, the rack 164*a*, the protrusion P1, the first push rod 140, the pulling component 145, the positioning trench S, the locking component 150, the driven portion P2, the positioning portion P3 and the elastic component E1 shown in FIG. 2 and FIG. 3, and descriptions thereof are not repeated herein.

Following the above, the glucose test device 200 differs from the glucose test device 100 in that the carrying unit 220 carries only the lancets 232 as shown in FIG. 10, different from the carrying unit 120 that carries both the lancets 132 and the test strips 134 as shown in FIG. 3. Correspondingly, the glucose test device 200 shown in FIG. 9 does not require the second push rod 190 shown in FIG. 2 for pushing test strips. That is, in the glucose test device 200, operation processes of the locking component 250, the gear set 264 of the first driving unit and the rack 264*a* of the gear set 264 are, e.g., the same as those of the locking component 150, the gear set 164 of the first driving unit and the rack 164*a* of the gear set 164 in FIG. 2. However, the gear set 264 of the first driving unit and the rack 264*a* of the gear set 264 are only configured to drive operation of the locking component 250 but not to drive operation of a second push rod.

Figure 11:
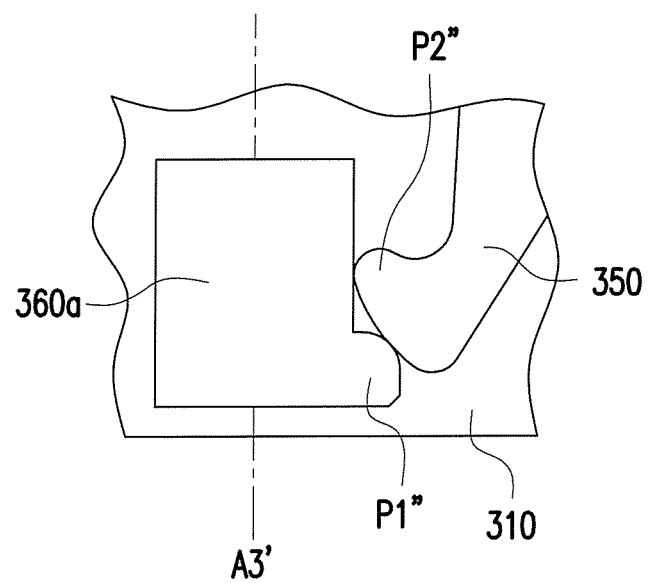
FIG. 11 is a schematic view of a first driving unit and a locking component according to still another embodiment of the invention.

FIG. 11 is a schematic view of a first driving unit and a locking component according to still another embodiment of the invention. A locking component 350 shown in FIG. 11 is disposed and operates in a similar manner to the locking component 250 shown in FIG. 9, and descriptions thereof are not repeated herein. The embodiment shown in FIG. 11 differs from the embodiment shown in FIG. 9 in that a first driving unit 360*a* in FIG. 11 does not drive the locking component 350 by a gear set. The first driving unit 360*a* is a solenoid valve, movably disposed at a casing 310 along a third axis A3', and drives the locking component 350 to be operated to the locking position or the releasing position through a protrusion P1'' thereof pushing a driven portion P2'' of the locking component 350, wherein the protrusion P1'' drives the driven portion P2'' in the same manner as the protrusion P1' drives the driven portion P2' in FIG. 9. In other embodiments, the first driving unit may be a driving source of other suitable types. The invention does not impose any limitation on this.

In summary, the glucose test device of the invention uses the carrying unit for containing a plurality of consumables (e.g., lancets and/or test strips) so as to replace the consumables with unused ones by means of the carrying unit for performing blood sampling and testing. Thus, a process of repeatedly installing the consumables is omitted, and further, convenience of operation of the glucose test device is enhanced. In addition, the glucose test device has the locking component disposed therein, and uses the control unit to automatically control the first driving unit to drive the locking component to lock or release the first push rod according to different operation conditions. Accordingly, the user is prevented from firing a lancet by the first push rod in an unexpected operation condition, and further, safety of use of the glucose test device is enhanced. Furthermore, the first driving unit is not only configured to drive the locking component to lock or release the first push rod, but also configured to drive the second push rod to push the test strip. Thus, the second push rod and the locking component share the same driving source (i.e., the first driving unit), thus saving the manufacturing cost of the glucose test device and disposition space therein. In addition, according to the type of the carrying unit being used (e.g., the carrying unit that carries both lancets and test strips, the carrying unit that carries only lancets or the carrying unit that carries only test strips), the control unit of the glucose test device of the invention correspondingly controls the glucose test device to operate in different manners, so that the glucose test device may apply the above three different types of carrying units.

Although the invention has been described with reference to the above embodiments, it will be apparent to persons of ordinary skill in the art that modifications to the described embodiments may be made without departing from the spirit of the invention. Accordingly, the scope of the invention will be defined by the attached claims and not by the above detailed descriptions.

What is claimed is:

1. A glucose test device, comprising:
a casing;
a carrying unit and a plurality of consumables, the carrying unit being disposed at the casing, the consumables being disposed in the carrying unit;
a first push rod movably disposed at the casing and aligned with the carrying unit, wherein the first push rod is suitable for moving to push one of the consumables out of the carrying unit;
a locking component movably disposed at the casing;
an elastic component, wherein the elastic component is connected between the first push rod and the casing, the first push rod is suitable for resisting an elastic force of the elastic component to move from an initial position to a loading position, and for moving from the loading position toward the carrying unit by the elastic force of the elastic component so as to push one of the consumables out of the carrying unit;
a pulling component, wherein the pulling component is movably disposed at the casing and has a pulling portion, and when the pulling component moves relative to the casing, the pulling component resists the elastic force of the elastic component to pull an end of the first push rod by the pulling portion, so that the first push rod moves from the initial position to the loading position;
a first driving unit connected to the locking component; and
a control unit electrically connected to the first driving unit, wherein the control unit is suitable for controlling the first driving unit to drive the locking component to be operated to a locking position so as to lock the first push rod as unmovable, and the control unit is suitable for controlling the first driving unit to drive the locking component to be operated to a releasing position so as to release the first push rod,
wherein the pulling component has a positioning trench, the locking component has a positioning portion, and when the locking component is located at the locking position, the positioning portion extends into the positioning trench to position the pulling component, so as to prevent the pulling component from pulling the first push rod,
wherein the consumables surround an axis, and the carrying unit is rotatably disposed around the axis to be driven by a second driving unit to align any one of the consumables with the first push rod.

2. The glucose test device of claim 1, wherein the first driving unit comprises a motor and a gear set, the gear set is connected between the motor and the locking component, and the motor is suitable for driving the gear set to be operated so as to drive the locking component to be operated to the locking position or the releasing position.

3. The glucose test device of claim 1, comprising a second push rod, wherein the second push rod is movably disposed at the casing and is aligned with the carrying unit, the second push rod is connected to the first driving unit, and when the consumables comprise a plurality of lancets and a plurality of test strips, the first push rod is suitable for moving to push one of the lancets out of the carrying unit, and the first driving unit is suitable for driving the second push rod to move toward the carrying unit so as to push one of the test strips out of the carrying unit.

4. The glucose test device of claim 3, wherein the first driving unit has a protrusion, the protrusion moves synchronously with the second push rod, the locking component has a driven portion, when the protrusion moves into a first moving range to be misaligned with the driven portion, the locking component is located at the locking position and the second push rod is separated from the carrying unit, when the protrusion moves into a second moving range to be aligned with the driven portion, the protrusion pushes the driven portion so that the locking component is operated to the releasing position and the second push rod is separated from the carrying unit, and when the protrusion moves into a third moving range to be misaligned with the driven portion, the locking component is operated to the locking position and the second push rod pushes one of the test strips out of the carrying unit, wherein the second moving range is located between the first moving range and the third moving range.

5. The glucose test device of claim 3, comprising the second driving unit, wherein the carrying unit has a plurality of first perforated grooves and a plurality of second perforated grooves, the lancets are disposed respectively in the first perforated grooves, the test strips are disposed respectively in the second perforated grooves, and the second driving unit is connected to the carrying unit and suitable for driving the carrying unit to rotate so as to align any one of the first perforated grooves with the first push rod and to align any one of the second perforated grooves with the second push rod.

6. The glucose test device of claim 1, comprising a second push rod, wherein the second push rod is movably disposed at the casing and is aligned with the carrying unit, the second push rod is connected to the first driving unit, and when the consumables comprise only a plurality of lancets, the first push rod is suitable for moving to push one of the lancets out of the carrying unit, and the first driving unit does not drive the second push rod to move toward the carrying unit.

7. The glucose test device of claim 1, comprising a second push rod, wherein the second push rod is movably disposed at the casing and is aligned with the carrying unit, the second push rod is connected to the first driving unit, and when the consumables comprise only a plurality of test strips, the first driving unit is suitable for driving the second push rod to move toward the carrying unit so as to push one of the test strips out of the carrying unit, and the locking component remains at the locking position.

8. The glucose test device of claim 1, wherein the glucose test device comprises a sensing unit, the sensing unit is electrically connected to the control unit and suitable for sensing a state of the carrying unit, wherein the state of the carrying unit comprises types of the consumables and a state of use of each of the consumables.

9. The glucose test device of claim 1, wherein after the first push rod pushes one of the consumables out of the carrying unit, the control unit controls the first driving unit to drive the locking component to be operated to the locking position, the glucose test device has an operation interface suitable for displaying a repeated firing option, and after the first push rod pushes one of the consumables out of the carrying unit and the first driving unit drives the locking component to be operated to the locking position, if the repeated firing option is executed, then the control unit controls the first driving unit to drive the locking component to be operated to the releasing position.

10. The glucose test device of claim 1, comprising a stopping component and a pressing component, wherein the stopping component is disposed at the casing and suitable for resisting the elastic force of the elastic component to stop the first push rod at the loading position, and the pressing component is disposed at the casing and suitable for being pressed to drive the stopping component to release the first push rod.

11. The glucose test device of claim 1, wherein the control unit has a first switch and a second switch, when the pulling component pulls the first push rod to move from the initial position to the loading position, the pulling component triggers the first switch, and when a pressing component is pressed to drive a stopping component to release the first push rod, the pressing component triggers the second switch, wherein after both the first switch and the second switch are triggered, the control unit controls the first driving unit to drive the locking component to be operated to the locking position.

12. The glucose test device of claim 1, wherein the pulling component comprises an outer casing and an adjusting element, the adjusting element is rotatably disposed at the outer casing and has an adjusting inclined plane, the pulling portion is movably disposed at the outer casing and has a flange, and the adjusting element is suitable for rotating to push the flange by the adjusting inclined plane so as to adjust a position of the pulling portion in the outer casing, such that a route of the first push rod toward the carrying unit is limited.

13. A glucose test device, comprising:
a casing;
a carrying unit and a plurality of consumables, the carrying unit being disposed at the casing, the consumables being disposed in the carrying unit;
a first push rod movably disposed at the casing and aligned with the carrying unit, wherein the first push rod is suitable for moving to push one of the consumables out of the carrying unit;
a locking component movably disposed at the casing;
a first driving unit connected to the locking component; and
a control unit electrically connected to the first driving unit, wherein the control unit is suitable for controlling the first driving unit to drive the locking component to be operated to a locking position so as to lock the first push rod as unmovable, and the control unit is suitable for controlling the first driving unit to drive the locking component to be operated to a releasing position so as to release the first push rod,
wherein after the first push rod pushes one of the consumables out of the carrying unit, the control unit controls the first driving unit to drive the locking component to be operated to the locking position, the glucose test device has an operation interface suitable for displaying a repeated firing option, and after the first push rod pushes one of the consumables out of the carrying unit and the first driving unit drives the locking component to be operated to the locking position, if the repeated firing option is executed, then the control unit controls the first driving unit to drive the locking component to be operated to the releasing position.

* * * * *